US006251136B1

(12) United States Patent
Guruwaiya et al.

(10) Patent No.: US 6,251,136 B1
(45) Date of Patent: Jun. 26, 2001

(54) METHOD OF LAYERING A THREE-COATED STENT USING PHARMACOLOGICAL AND POLYMERIC AGENTS

(75) Inventors: Judy A. Guruwaiya; Deborra Sanders Millare, both of San Jose; Steven Z-H Wu, Santa Clara, all of CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/457,195

(22) Filed: Dec. 8, 1999

(51) Int. Cl.[7] .................................................. A61F 2/06
(52) U.S. Cl. ............................................................ 623/1.46
(58) Field of Search .................. 623/1.15, 1.44–1.48, 623/1, 901, 12; 424/422–425; 604/265–266

(56) References Cited

U.S. PATENT DOCUMENTS

| | | |
|---|---|---|
| 4,239,754 | 12/1980 | Sache et al. . |
| 4,241,046 | 12/1980 | Papahadjopoulos et al. . |
| 4,299,613 | 11/1981 | Cardarelli . |
| 4,346,028 | 8/1982 | Griffith . |
| 4,348,329 | 9/1982 | Chapman . |
| 4,355,426 | 10/1982 | MacGregor . |
| 4,400,374 | 8/1983 | Cardarelli . |
| 4,441,215 | 4/1984 | Kaster . |
| 4,633,873 | 1/1987 | Dumican et al. . |
| 4,678,660 | 7/1987 | McGary et al. . |
| 4,689,386 | 8/1987 | Chapman et al. . |
| 4,718,907 | 1/1988 | Karwoski et al. . |

(List continued on next page.)

FOREIGN PATENT DOCUMENTS

| | | |
|---|---|---|
| 0 452 995 A2 | 10/1991 | (EP) . |
| 0 499 299 A3 | 8/1992 | (EP) . |
| 0 551 182 A1 | 7/1993 | (EP) . |
| 0 567 788 A1 | 11/1993 | (EP) . |
| 0 604 022 A1 | 6/1994 | (EP) . |
| 0 621 017 A1 | 10/1994 | (EP) . |
| 0 649 637 A1 | 4/1995 | (EP) . |
| WO 87/02684 | 5/1987 | (WO) . |
| WO 91/17789 | 11/1991 | (WO) . |
| WO 94/13268 | 6/1994 | (WO) . |
| WO 96/28115 | 9/1996 | (WO) . |

OTHER PUBLICATIONS

Casper, R.A., et al., Fiber–Reinforced Absorbable Composite for Orthopedic Surgery, *Polymeric Materials Science and Engineering*, pp. 497–501, vol. 53 (Fall 1985).

Kelley, Benjamin S., et al., Totally Resorbable High–Strength Composite Material, *Polymer Science Technology: Advances in Biomedical Polymers* (Edited by Charles G. Gebelein), pp. 75–85, vol. 35, 1987.

Schatz, Richard A., M.D., A View of Vascular Stents, *Circulation*, pp. 445–457, vol. 79, 1989.

Muller, David W.M., et al., Advances in Coronary Angioplasty: Endovascular Stents, *Coronary Artery Disease*, vol. 1, No. 4, pp. 438–447, Jul./Aug. 1990.

Wong, Shing–Chiu, M.D., et al., An Update on Coronary Stents, *Cardio*, pp. 30–50, Feb. 1992.

(List continued on next page.)

*Primary Examiner*—Cary E. O'Connor
(74) *Attorney, Agent, or Firm*—Fulwider Patton Lee & Utecht, LLP

(57) ABSTRACT

A pharmacological agent is applied to a stent in dry, micronized form over a sticky base coating. A membrane forming polymer, selected for its ability to allow the diffusion of the pharmacological agent therethrough, is applied over the entire stent. More specifically, a stent, typically a metal stent, has a layer of a sticky material applied to selected surfaces of the stent. A pharmacological agent is layered on the sticky material and a membrane forming a polymer coating is applied over the pharmacological agent. The membrane is formed from a polymer that permits diffusion of the pharmacological agent over a predetermined time period.

23 Claims, 1 Drawing Sheet

U.S. PATENT DOCUMENTS

| | | |
|---|---|---|
| 4,721,800 | 1/1988 | Chapman et al. . |
| 4,722,335 | 2/1988 | Vilasi . |
| 4,723,549 | 2/1988 | Wholey et al. . |
| 4,732,152 | 3/1988 | Wallstén et al. . |
| 4,733,665 | 3/1988 | Palmaz . |
| 4,739,762 | 4/1988 | Palmaz . |
| 4,776,337 | 10/1988 | Palmaz . |
| 4,792,599 | 12/1988 | Durrani . |
| 4,816,339 | 3/1989 | Tu et al. . |
| 4,877,030 | 10/1989 | Beck et al. . |
| 4,878,906 | 11/1989 | Lindemann et al. . |
| 4,879,135 | 11/1989 | Greco et al. . |
| 4,902,290 | 2/1990 | Fleckenstein et al. . |
| 4,937,369 | 6/1990 | Chapman et al. . |
| 5,015,238 | 5/1991 | Solomon et al. . |
| 5,026,377 | 6/1991 | Burton et al. . |
| 5,059,211 | 10/1991 | Stack et al. . |
| 5,061,254 | 10/1991 | Karakelle et al. . |
| 5,062,829 | 11/1991 | Pryor et al. . |
| 5,084,065 | 1/1992 | Weldon et al. . |
| 5,085,629 | 2/1992 | Goldberg et al. . |
| 5,104,403 | 4/1992 | Brotzu et al. . |
| 5,108,755 | 4/1992 | Daniels et al. . |
| 5,128,408 | 7/1992 | Tanaka et al. . |
| 5,135,516 | 8/1992 | Sahatjian et al. . |
| 5,151,105 | 9/1992 | Kwan-Gett . |
| 5,156,623 | 10/1992 | Hakamatsuka et al. . |
| 5,163,951 | 11/1992 | Pinchuk et al. . |
| 5,163,952 | 11/1992 | Froix . |
| 5,163,958 | 11/1992 | Pinchuk . |
| 5,180,366 | 1/1993 | Woods . |
| 5,192,311 | 3/1993 | King et al. . |
| 5,197,977 | 3/1993 | Hoffman, Jr. et al. . |
| 5,234,456 | 8/1993 | Silvestrini . |
| 5,234,457 | 8/1993 | Andersen . |
| 5,236,447 | 8/1993 | Kubo et al. . |
| 5,279,594 | 1/1994 | Jackson . |
| 5,282,860 | 2/1994 | Matsuno et al. . |
| 5,289,831 | 3/1994 | Bosley . |
| 5,290,271 | 3/1994 | Jernberg . |
| 5,306,286 | 4/1994 | Stack et al. . |
| 5,330,500 | 7/1994 | Song . |
| 5,342,348 | 8/1994 | Kaplan . |
| 5,342,621 | 8/1994 | Eury . |
| 5,356,433 | 10/1994 | Rowland et al. . |
| 5,370,684 | 12/1994 | Vallana et al. . |
| 5,380,299 | 1/1995 | Fearnot et al. . |
| 5,383,925 | 1/1995 | Schmitt . |
| 5,383,927 | 1/1995 | De Goicoechea et al. . |
| 5,383,928 | 1/1995 | Scott et al. . |
| 5,385,580 | 1/1995 | Schmitt . |
| 5,571,187 | 11/1996 | Devanathan . |
| 5,607,463 * | 3/1997 | Schwartz et al. ............... 623/1 |
| 5,624,411 | 4/1997 | Tuch . |
| 5,630,840 | 5/1997 | Mayer . |
| 5,632,779 | 5/1997 | Davidson . |
| 5,662,712 * | 9/1997 | Pathak et al. ............... 623/1 |
| 5,697,967 | 12/1997 | Dinh et al. . |
| 5,716,981 * | 2/1998 | Hunter et al. ............... 623/1 |
| 5,725,567 | 3/1998 | Wolff et al. . |
| 5,733,327 | 3/1998 | Igaki et al. . |
| 5,743,875 | 4/1998 | Sirhan et al. . |
| 5,749,888 | 5/1998 | Yock . |
| 5,768,507 | 6/1998 | Fischell et al. . |
| 5,797,887 * | 8/1998 | Rosen et al. ............... 604/265 |
| 5,837,313 | 11/1998 | Ding et al. . |
| 5,843,172 | 12/1998 | Yan . |
| 5,876,433 * | 3/1999 | Lunn ............... 623/1 |
| 5,879,697 * | 3/1999 | Ding et al. ............... 623/1 |
| 5,891,108 | 4/1999 | Leone et al. . |
| 5,891,507 | 4/1999 | Jayaraman . |

OTHER PUBLICATIONS

Lambert, Thomas L., M.D., et al., Localized Arterial Wall Drug Delivery From a Polymer–Coated Removable Metallic Stent: Kinteics, Distribution, and Bioactivity of Forskolin, *Circulation*, pp. 1003–1011, vol. 90, No. 2, Aug. 1994.

Eury, Robert P., Multilayered Biodegradable Stent and Method for its Manufacture, *Chemical Abstracts*, vol. 121, No. 9, 117810, Aug. 29, 1994.

Eury, Robert P., Antithrombogenic Surface, *Chemical Abstracts*, vol. 121, No. 17, 213062, Aug. 29, 1994.

De Scheerder, Ivan K., et al., Biocompaticility of Polymer–Coated Oversized Metallic Stents Implanted in Normal Porcine Coronary Arteries, *Atherosclerosis*, pp. 105–114, vol. 114, 1995.

Christos, Jason, et al., Development of a Model for r.f. PE–CVD–Deposited Fluoropolymer Films Using $C_3F_6$, *Journal of Undergraduate Research in Engineering*, pp. 52–64, undated.

Sarma, S., Bovine Aortic Endothelial Cell Growth on Fluorocarbon FRGD Plasma Films, *Journal of Undergraduate Research in Engineering*, pp. 115–131, undated.

* cited by examiner

METHOD OF LAYERING A THREE-COATED STENT USING PHARMACOLOGICAL AND POLYMERIC AGENTS

BACKGROUND OF THE INVENTION

This invention relates generally to expandable intraluminal vascular grafts, commonly referred to as stents, and more particulary pertains to the coating of stents with materials that allow for the controlled release of pharmacological agents.

Stents are implanted within vessels in an effort to maintain the patency thereof by preventing collapse and/or impeding restenosis. Implantation of a stent is typically accomplished by mounting the stent on the expandable portion of a balloon catheter, maneuvering the catheter through the vasculature so as to position the stent at the treatment site within the body lumen, and inflating the balloon to expand the stent so as to engage the lumen wall. The stent deforms in the expanded configuration allowing the balloon to be deflated and the catheter removed to complete the implantation procedure. The use of self-expanding stents obviates the need for a balloon delivery device. Instead, a constraining sheath that is initially fitted about the stent is simply retracted once the stent is in position adjacent the treatment site. Stents and stent delivery catheters are well known in the art.

The success of a stent placement can be assessed by evaluating a number of factors, such as thrombosis, neointimal hyperplasia, smooth muscle cell migration and proliferation following implantation of the stent, injury to the artery wall, overall loss of luminal patency, stent diameter in vivo, thickness of the stent, and leukocyte adhesion to the luminal lining of stented arteries. The chief areas of concern are early subacute thrombosis, and eventual restenosis of the blood vessel due to intimal hyperplasia.

Therapeutic pharmacological agents have been developed to address some of the concerns associated with the placement of a stent and it is often desirable to provide localized pharmacological treatment of a vessel at the site being supported by the stent. It has been found convenient to utilize the implanted stent for such purpose wherein the stent serves both as a support for the lumen wall as a well as delivery vehicle for the pharmacological agent. However, the metallic materials typically employed in the construction of stents in order to satisfy the mechanical strength requirements are not generally capable of carrying and releasing drugs. On the other hand, while various polymers are known that are quite capable of carrying and releasing drugs, they generally do not have the requisite strength characteristics. Moreover, the structural and mechanical capabilities of a polymer may be significantly reduced as such polymer is loaded with a drug. A previously devised solution to such dilemma has therefore been the coating of a stent's metallic structure with a drug carrying polymer material in order to provide a stent capable of both supporting adequate mechanical loads as well as delivering drugs.

Various approaches have previously been employed to join drug-carrying polymers to metallic stents including for example dipping, spraying and conforming processes. Additionally, methods have been disclosed wherein the metallic structure of the stent has been formed or treated so as to create a porous surface that enhances the ability to retain the applied materials. However, such methods have generally failed to provide a quick, easy and inexpensive way of loading drugs onto a stent, have been limited insofar as the maximum amount of drug that can be loaded onto a stent and are limited in terms of their ability to control the rate of release of the drug upon implantation of the stent. Additionally, some of the heretofore known methods are highly specific wherein they are substantially limited in terms of which underlying stent material the coating can be applied to.

SUMMARY OF THE INVENTION

The present invention overcomes the shortcomings of the prior art methods for loading a drug onto a stent. The process enables large amounts of one or more drugs to be quickly and easily loaded onto the stent and provides for the subsequent release of such drug at a very controlled rate. A stent constructed in accordance with the present invention is capable of releasing substantially greater dosages of drugs at substantially more controlled release rates than has heretofore been possible. Moreover, the present invention allows for the drug releasing materials to be applied to any stent construction material.

The method of the present invention requires the sequential application of three layers of different materials onto a stent's surfaces. A first layer is applied to all or to selected surfaces of a stent and serves as a base or primer coat which readily adheres to the material of which the stent is constructed and in turn, is able to attract and retain the subsequently applied pharmacological agent. Such pharmacological agent, in the form of dry, micronized particles is dusted directly onto all or onto only selected surfaces of the base layer coated stent to form a second layer. A membrane forming polymer is subsequently applied over the coated stent surfaces wherein such polymer is selected for its ability to permit the diffusion of the pharmacological agent therethrough.

The base layer material is selected for its ability to form a sticky coating on the particular material used in the construction of the stent. Such first layer may be applied to all or selected surfaces of the stent. The pharmacological material is used in a dry, micronized form which allows the amount of material applied to the base layer to be precisely controlled. The top layer material is selected for its ability to form a membrane over the entire surface of the stent be it the bare stent material, the base layer coat or the pharmacological agent, and for its ability to permit the diffusion of the pharmacological agent therethrough. The amount of pharmacological material deposited in the second layer determines the total dosage that can delivered while the thickness of the top layer determines the rate of delivery.

The particular surface or surfaces on which the pharmacological agent is deposited determines where the agent is delivered upon implantation. More specifically, pharmacological material deposited on the exterior surfaces of the stent causes the agent to pass directly into the lumen wall while deposition of the agent on the interior surfaces of the stent causes the agent to be released directly into the blood flow. Alternatively, coating only the upstream edge or only the downstream edge of the stent may be desirable to achieve a specific effect. By selectively coating the stent surfaces with the base layer, the distribution of the pharmacological agent may be controlled accordingly as the dry particles will only adhere to those areas that have the sticky coating. Alternatively, the entire stent may be base coated while the application of the pharmacological agent is precisely controlled by limiting its distribution to only preselected areas. Well known masking techniques may be used for such purpose. The membrane forming material may be applied by any well known technique such as for example by dipping or spraying while material is in its liquid form. Allowing the material to form a continuous membrane completes the fabrication process.

These and other features and advantages of the present invention will become apparent from the following detailed description of preferred embodiments which, taken in conjunction with the accompanying drawings, illustrate by way of example the principles of the invention.

DETAILED DESCRIPTION OF THE PREFERRED EMBODIMENTS

The stent constructed in accordance with the present invention is employed as a drug delivery device which is implanted in the body and may simultaneously serve to support the body lumen at the deployment site. The present invention is not limited to any particular stent configuration or delivery method nor is the construction of the stent structure limited to the use of any particular construction material.

Figure 1:
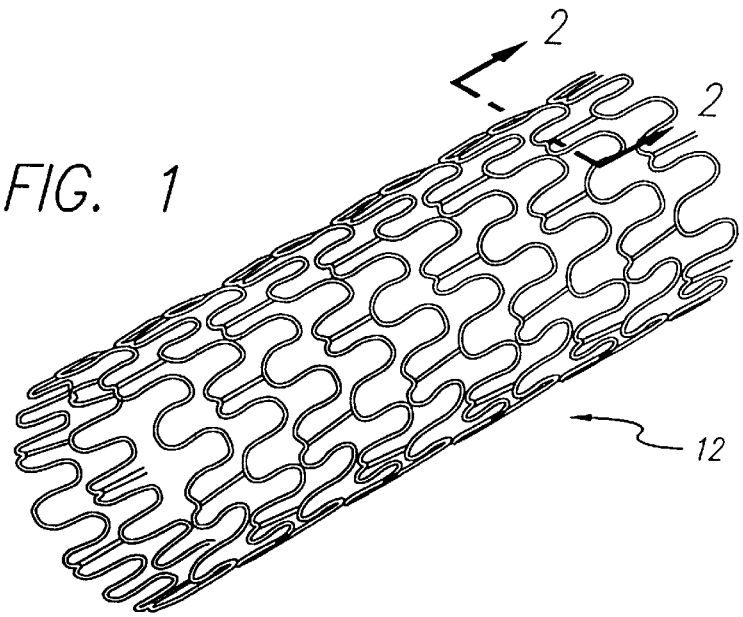
FIG. 1 is a perspective view of a stent.

FIG. 1 is a perspective view generally depicting a stent 12. Such view is not intended to represent any particular stent configuration or structure but is merely provided to put into context the cross-sectional views of the various embodiments shown in FIGS. 2–4.

Figure 2:
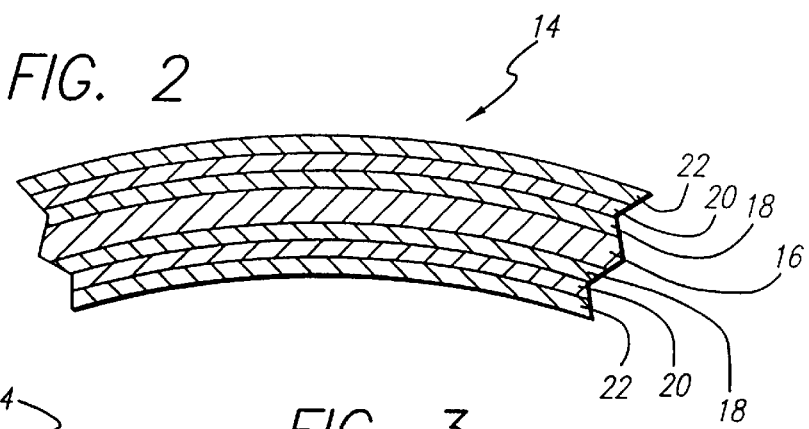
FIG. 2 is a greatly enlarged cross-sectional view, such as taken along lines 2—2 of FIG. 1, of a stent fabricated in accordance with the present invention.

FIG. 2 shows an embodiment 14 of the present invention wherein the underlying structure of the stent 16 has a total of three layers of materials coated onto all of its surfaces. A first layer, or base coat 18 is shown applied directly to the surfaces of the stent upon which a second layer, comprising a pharmacological agent 20, is applied. A third layer, in the form of a continuous membrane 22, encapsulates the entire device.

The base coat 18 serves as a primer by readily adhering to the underlying stent's surfaces and then readily accepting and retaining a pharmacological agent applied thereto. The base coat material may consist of vitronectin, fibronectin, gelatin, collagen or the like. Such materials are readily available, are relatively inexpensive and dry to form a sticky coating. The desired stickiness is achieved with the application of a very thin even coating of the base coat on the stent which serves to minimize the overall wall thickness of the device and further has the desirable effect of minimizing the amount of webbing that forms between adjacent structural components of the stent. The base layer may be applied by any of several methods including for example dipping, spraying, sponging or brushing. In the embodiment illustrated in FIG. 2, the underlying stent structure is simply dipped or submerged in the base coat material while in its liquid form to uniformly coat all surfaces of the stent. The dipping solution should not dissolve the drug particles. Upon drying or curing, all exposed surfaces of the stent remain sticky.

The pharmacological agent 20 is supplied in the form of dry, micronized particles that readily adhere to the sticky base layer surface. A variety of pharmacological agents are commercially available in such form having a preferred particle size of about 1 to 0.5 microns. Examples of such agents include but are not limited to antibiotic, anti-thrombotic and anti-restenotic drugs. Additionally, any such micronized agents can be combined in any of various combinations in order to dispense a desired cocktail of pharmacological agents to the patient. For example, a number of different pharmacological agents can be combined in each micronized particle. Alternatively, micronized particles of individual pharmacological agents can be intermixed prior to application to the sticky base layer. As a further alternative, different pharmacological agents can be applied to different surfaces of the stent. In the particular embodiment illustrated, the micronized particles are applied to all surfaces of the base coated stent wherein such application may be achieved by any of a number of well known methods. For example, the particles may be blown onto the sticky surface or optionally, may simply be rolled in the powder. The former approach allows the total amount of pharmacological agent that is to be applied to the stent to be precisely controlled.

The outer membrane 22 encapsulates the entire stent to cover all of its surfaces, including any bare stent structure, any exposed base coating or the layer of micronized drug particles. The material is selected for its membrane forming characteristic and its biocompatiblity as well as its permeability to the pharmacological agent. The chemical composition of the membrane forming polymer and that of the pharmacological agent in combination with the thickness of the applied outer layer will determine the diffusion rate of the pharmacological agent. An example of a suitable material is ethylene vinyl alcohol into which the base coated and pharmacological agent carrying stent may simply be dipped. The ethylene vinyl alcohol forms the desired membrane upon curing.

Alternatively, fluorocarbon films may be employed to serve as the outer layer in the stent of the present invention. Such films have been successfully used as drug-delivery capsules and are capable of serving a similar function when applied about the exterior of the stent of the present invention. A representative example of such film is described in the paper entitled *Development of a Model for r.f. PE-CVD-Deposited Fluoropolymer Films Using C3F6* by Jason Christos, et al in the *Journal of Undergraduate Research in Engineering,* page 52.

Figure 3:
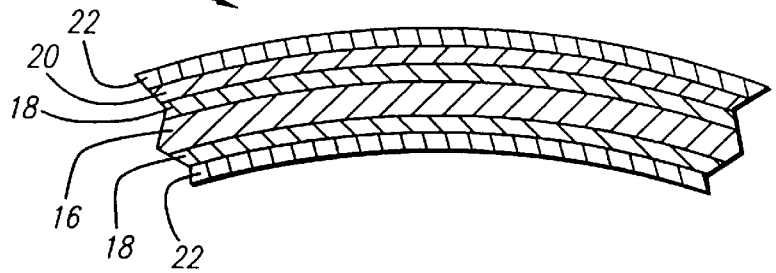
FIG. 3 is a greatly enlarged cross-sectional view of an alternative embodiment stent fabricated in accordance with the present invention.

FIG. 3 illustrates an alternative embodiment 24 of the present invention. The underlying stent structure, base layer, pharmacological agent and outer membrane layer are identified by the same reference numerals employed in FIG. 2. In this particular embodiment, the base layer 18 is again applied to all surfaces of the underlying stent structure 16 while the pharmacological agent 20 is applied to only selected surfaces. This is achieved by masking those areas in which no pharmacological agent is to become adhered to the sticky base layer. In the particular embodiment that is illustrated, only the exterior surface has the pharmacological agent adhered thereto. Alternatively, a second, different pharmacological agent may be applied to the interior surface of the stent such that a single stent serves to dispense a first pharmacological agent into the lumen walls while the second agent is simultaneously dispensed into the blood flow. In either embodiment, the outer membrane 22 covers the entire stent.

Figure 4:
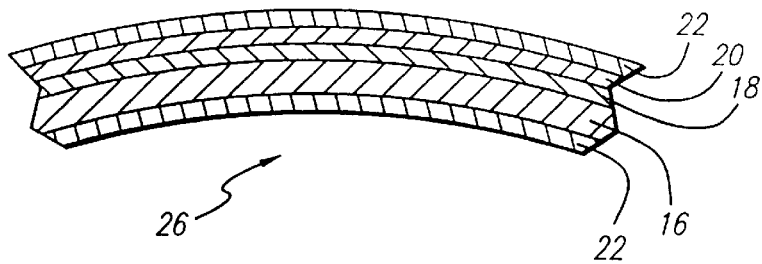
FIG. 4 is a greatly enlarged cross-sectional view of another alternative embodiment stent fabricated in accordance with the present invention.

FIG. 4 illustrates another alternative embodiment 26 of the present invention. The underlying stent structure, base layer, pharmacological agent and outer membrane layers are again identified by the same reference numerals employed in FIGS. 2 and 3. In this particular embodiment the base layer 18 is selectively applied to various surface of the underlying stent structure 16. This achieved by masking those areas were no base layer and consequently no pharmacological agent 20 is to be present. The illustration shows the base layer as being exclusively applied to the exterior surface of the stent. Any of a variety of masking techniques can be employed to achieve the selective coating pattern. The subsequently applied pharmacological agent in the form of dry, micronized particles, only adheres to those surfaces having the sticky base layer coating. The outer membrane forming layer 22 is again applied to all surfaces.

In use, the stent is deployed using conventional techniques. Once in position the pharmacological agent gradually diffuses into the adjacent tissue at a rate dictated by the parameters associated with the applied outer membrane. The total dosage that is delivered is of course limited by the total amount of pharmacological agent that had been loaded onto the stent's various surfaces. The pharmacological agent is selected to treat the deployment site and/or locations downstream thereof. For example, deployment in the carotid artery will serve to deliver such agent to the brain.

While a particular form of the invention has been illustrated and described, it will also be apparent to those skilled in the art that various modifications can be made without departing from the spirit and scope of the invention. Accordingly, it is not intended that the invention be limited except by the appended claims.

What is claimed:

1. A method for coating a stent, comprising the steps of:
   providing a stent;
   applying a base layer of sticky material to selected surfaces of said stent;
   applying pharmacological agent in micronized, dry form to selected surfaces coated by said base layer; and
   applying a membrane forming polymer coating through which said pharmacological agent is able to diffuse to all surfaces of said stent.

2. The method of claim 1, wherein said base layer is applied to all surfaces of said stent.

3. The method of claim 1, wherein said stent is masked so as to limit application of said base layer to only selected surfaces of said stent.

4. The method of claim 1, wherein said pharmacological agent is applied to all surfaces having said base layer applied thereto.

5. The method of claim 1, wherein said stent is masked so as to limit application of said pharmacological agent to only selected surfaces coated with said base coat.

6. The method of claim 1, wherein a plurality of pharmacological agents are applied to selected surfaces having said base layer applied thereto.

7. The method of claim 6, wherein said plurality of pharmacological agents comprises a uniform mixture.

8. The method of claim 6, wherein selected pharmacological agents of said plurality of pharmacological agents are applied.

9. The method of claim 1, wherein, the base layer is selected from the group consisting of vitronectin, fibronectin, gelatin and collagen.

10. The method of claim 1, wherein said base layer is applied by dipping.

11. The method of claim 1, wherein said pharmacological agent is applied by rolling said stent in a mass of said pharmacological agent.

12. The method of claim 1, wherein said pharmacological agent is applied by blowing said dry, micronized particles onto said stent.

13. The method of claim 1, wherein said membrane forming polymer comprises ethylene vinyl acetate.

14. The method of claim 1, wherein said membrane forming polymer comprises a fluoropolymer film.

15. A coated stent, comprising:
    an expandable structure;
    a base coating of sticky material;
    an intermediate coating of pharmacological agent in dry, micronized form; and
    an outer coating of membrane forming polymer through which said pharmacological agent is capable of diffusing.

16. The coated stent of claim 15, wherein said base coating is present on only selected surfaces of said expandable structure.

17. The coated stent of claim 15, wherein said pharmacological agent is present on only selected base coated surfaces.

18. The coated stent of claim 15, wherein said intermediate coating comprises a plurality of pharmacological agents.

19. The coated stent of claim 15, wherein said plurality of pharmacological agents is homogeneously distributed throughout said intermediate coating.

20. The coated stent of claim 15, wherein said plurality of pharmacological agents is heterogeneously distributed throughout said intermediate coating.

21. The coated stent of claim 17, wherein said expandable structure has exterior surfaces and interior surfaces and wherein a first of said plurality of pharmacological agents is distributed on said exterior surfaces and a second of said pharmacological agents is distributed on said interior surfaces.

22. The coated stent of claim 15, wherein said outer coating comprises ethylene vinyl acetate.

23. The coated stent of claim 15, wherein said outer coating comprises a fluoropolymer film.

* * * * *

UNITED STATES PATENT AND TRADEMARK OFFICE
CERTIFICATE OF CORRECTION

PATENT NO. : 6,251,136 B1           Page 1 of 1
DATED : June 26, 2001
INVENTOR(S) : Judy A. Guruwaiya, et al.

It is certified that error appears in the above-identified patent and that said Letters Patent is hereby corrected as shown below:

<u>Title page,</u>
Under "FOREIGN PATENT DOCUMENTS", add the following:
-- WO 93/06792      4/1993      (WO) --.

Signed and Sealed this

Nineteenth Day of February, 2002

*Attest:*

JAMES E. ROGAN
*Attesting Officer*     *Director of the United States Patent and Trademark Office*